United States Patent [19]
Dorian et al.

[11] Patent Number: 5,643,594
[45] Date of Patent: Jul. 1, 1997

[54] SPIN ENCAPSULATION APPARATUS AND METHOD OF USE

[75] Inventors: Randel E. Dorian, Orinda; Kent C. Cochrum, Davis; Richard David Antanavich, Paso Robles, all of Calif.

[73] Assignee: The Regents of the University of California, Oakland, Calif.

[21] Appl. No.: 237,290

[22] Filed: May 3, 1994

Related U.S. Application Data

[63] Continuation-in-part of Ser. No. 891,564, May 29, 1992, Pat. No. 5,429,821, and Ser. No. 186,327, Jan. 24, 1994, Pat. No. 5,578,314.

[51] Int. Cl.$^6$ .................. A61F 2/02; A01N 1/02; C12N 11/02; B29C 39/10
[52] U.S. Cl. .......... 424/424; 435/1.1; 435/177; 435/178; 435/179; 435/180; 435/182; 435/366; 435/382; 623/11; 425/8; 425/10; 425/804; 264/4; 264/7; 264/8; 264/DIG. 37
[58] Field of Search .................. 424/423, 424; 435/1, 177, 178, 179, 180, 182, 240.22, 240.241, 240.243; 623/11; 425/8, 10, 804; 264/8, 7, 4, DIG. 37

[56] References Cited

U.S. PATENT DOCUMENTS

| | | | |
|---|---|---|---|
| 1,671,866 | 5/1928 | Linville et al. | 425/8 |
| 2,439,772 | 4/1948 | Gow | 264/8 |
| 2,955,956 | 10/1960 | Baugh et al. | 117/100 |
| 3,015,128 | 1/1962 | Somerville, Jr. | 264/DIG. 37 |
| 3,429,295 | 2/1969 | Shapiro | 118/49.1 |
| 3,721,511 | 3/1973 | Schlienger | 264/8 |
| 3,743,464 | 7/1973 | Strobert | 425/8 |
| 3,870,014 | 3/1975 | Buck | 118/52 |
| 4,218,409 | 8/1980 | Dannelly | 264/8 |
| 4,298,476 | 11/1981 | Dudley | 210/373 |
| 4,311,570 | 1/1982 | Cowen et al. | 425/8 |
| 4,318,941 | 3/1982 | Gillett et al. | 427/212 |
| 4,352,883 | 10/1982 | Lim | 435/178 |
| 4,386,895 | 6/1983 | Sodickson | 425/5 |
| 4,391,909 | 7/1983 | Lim | 435/178 |
| 4,407,957 | 10/1983 | Lim | 435/178 |
| 4,409,331 | 10/1983 | Lim | 435/178 |
| 4,663,286 | 5/1987 | Tsang | 435/178 |
| 4,673,566 | 6/1987 | Goosen et al. | 424/19 |
| 4,675,140 | 6/1987 | Sparks et al. | 264/4.3 |
| 4,689,293 | 8/1987 | Goosen et al. | 435/1 |
| 4,749,620 | 6/1988 | Rha et al. | 428/402.2 |
| 4,764,317 | 8/1988 | Anderson et al. | 264/4 |
| 4,800,160 | 1/1989 | Iguchi et al. | 435/177 |
| 4,803,168 | 2/1989 | Jarvis, Jr. | 435/240.22 |
| 4,806,355 | 2/1989 | Goosen et al. | 424/424 |
| 4,824,478 | 4/1989 | Roberts et al. | 425/8 |
| 4,902,295 | 2/1990 | Walthall et al. | 623/11 |
| 4,997,443 | 3/1991 | Walthall et al. | 623/11 |
| 5,061,520 | 10/1991 | Hermelin | 427/212 |
| 5,124,090 | 6/1992 | Shimizu et al. | 425/8 |

FOREIGN PATENT DOCUMENTS

| | | | |
|---|---|---|---|
| 2034641 | 5/1992 | Canada . | |
| 1018808 | 5/1983 | U.S.S.R. | 425/8 |

*Primary Examiner*—Carlos Azpuru
*Attorney, Agent, or Firm*—Hana Verny

[57] ABSTRACT

A coating apparatus includes a rotary cup for forming beads and projecting them radially outwardly, and one or more collection basins surrounding the bead forming cup. The cup is adjustably rotatable about its central axis, and the collection basins are independently rotatable and positioned to collect the beads projected from the cup. The coating apparatus further includes an elevation adjustment system for axially adjusting the alignment of the cup with respect to the selected collection basins. The rotational speeds of the cup and the collection basins are selected so as to minimize the impact of the beads against a gelling solution in the collection basins. In use, a supply mixture is introduced into a mixing chamber of the cup. As the cup spins, the coated particles are propelled upwardly by the centrifugal force from the mixing chamber along the inner surface of the cup, and are projected radially outwardly, as beads, into the gelling solution in one of the selected basins. Since the cup and the basin are simultaneously rotated, the impact of the beads against the capture solution is significantly reduced.

37 Claims, 6 Drawing Sheets

SPIN ENCAPSULATION APPARATUS AND METHOD OF USE

CROSS-REFERENCE TO RELATED APPLICATIONS

This is a continuation-in-part of the application Ser. No. 07/891,564, filed May 29, 1992, now U.S. Pat. No. 5,429,821, and application Ser. No. 08/186,327, filed Jan. 24, 1994, now U.S. Pat. No. 5,578,314. This application also relates to the application Ser. No. 08/185,709, filed Jan. 24, 1994, now U.S. Pat. No. 5,521,079.

BACKGROUND OF THE INVENTION

1. Field of the Invention

The present invention is directed to a method and apparatus for coating biological materials such as tissues, cells and cell lines with a thin semi-permeable, bio-compatible coating. More particularly, this invention relates to a spin encapsulation apparatus and method for providing thin continuous coatings of the biological material and other solid and semi-solid particles such as pancreatic islet cells, to form smooth and uniform microcapsules.

BACKGROUND ART AND RELATED ART DISCLOSURES

Coating or microencapsulation of solid particles in general, and biological materials in particular, is widely employed to protect the encapsulated substances from environmental effects, to control their release time, and to confer improved handling characteristics. Typical substances which are coated or microencapsulated are drugs and biological materials such as tissues, cells and cell lines.

Conventional medical treatments for functional deficiencies of secretory and other biological organs have focused on replacing identified normal products of the deficient organ with natural or synthetic pharmaceutical compositions. For example, for treating insulin-dependent diabetes mellitus, also known as type I or juvenile onset diabetes, the normal secretion of insulin by the islets of Langerhans in the pancreas must be replaced, since functional islets are no longer present in the pancreas. This pancreatic function is emulated by administering insulin, titrating the injections in response to blood glucose level measurements. At best, the normal production of the islets is poorly approximated.

Organ replacement has also been applied. This has generally required continuous use of immunosuppressive agents to prevent immunological rejection of the organ, depriving the patient of the full protective function of the immune system against diseases. It has provided permanent relief only for a limited group of organs.

Attempts to transplant organ tissues into genetically dissimilar hosts without immunosuppression have been generally defeated by the immune system of the host. The application of effective protective barrier coatings to isolate the transplant tissues from the host immune system has not proven to be medically practical for a number of reasons. The coating materials were incompatible with the host system or unsuitable for other reasons. Encapsulation or coating processes previously developed did not yield reproducible coatings having the desired permeability and thickness required for the transplant tissue to have a long and effective functioning life in the host.

To protect transplants from destruction by the immune response of the host animal, various attempts have been made to create a protective barrier between the transplant tissue or cells and the immunological components of the host's system. T. M. S. Chang, Science 146: 524–525 (1964) described the microencapsulation of erythrocyte hemolysate and urease in semipermeable polyamide membranes. These microcapsules did not survive for long when injected into the blood stream. K. Mosbach et al, Acta Chem.Scand. 20:2807–2812 (1966) and T. M. S. Chang et al, Can. J. Physiol. and Pharmacology 44:115–128 (1966) described the preparation of semi-permeable microencapsulated microbial cells and viable red blood cells, the latter article mentioning the possibility of using injections of encapsulated cells for organ replacement therapy.

Numerous other conventional coating or microencapsulation techniques have been developed. By and large, these techniques suffer from the inability to precisely control the thickness of the coating and the overall diameter of the microcapsules, while maintaining the ability to efficiently generate one or multiple coatings with smooth outer surfaces. The following patents exemplify these conventional techniques: U.S. Pat. No. 4,386,895 to Sodickson, U.S. Pat. No. 4,675,140 to Sparks et al., and U.S. Pat. No. 4,800,160 to Iguchi et al.

The Sodickson patent discloses a capsule forming apparatus having an elaborate design of reservoirs and conduits. The capsule forming apparatus includes a rotor assembly which defines a gelling agent reservoir, and a rotor having a central axis of rotation. The rotor assembly is connected to a motor and a drive shaft. When the motor is actuated, the rotor assembly rotates about its axis. The rotor consists of a disc-shaped block having four radial vanes, and defines two concentric circular reservoirs 34, 36 and an opening 38 coaxial to the rotor axis. A pair of conduits 39 are spaced apart by 180 degrees adjacent to the bottom of the reservoir 34, for communication with two radial tubes 40. The reservoir 34 and its associated conduits serve to replenish the gelling agent during the production of microcapsules.

Several radial conduits 42 are disposed near the bottom of the reservoir 36, and communicate with a bundle of radial hollow needles 44. Four ducts 50–56 are disposed next to the central opening 38 and communicate with microcapsule-collecting tubes 58–64, and with yet another reservoir 82. The rotor assembly includes a vertical sidewall 68. In operation, the gelling agent is placed in the reservoir 82 and a suspension is placed in the reservoir 36. When the rotor assembly is caused to rotate, the liquid gelling agent in the reservoir 82 is centrifugally urged to form a layer 15–25 mm thick on the sidewall 68. Simultaneously, the gellable liquid and core material in the reservoir 36 are centrifugally urged through the conduits 42 and needles 44. As the liquid passes out of the needles 44, it breaks up into droplets which are propelled radially across a 2–5 mm gap to the layer of gelling agent, where they are gelled.

The Sparks et al. patent describes another method of coating particles by feeding a suspension of two materials onto a rotating disc. The suspension is centrifugally dispersed by the rotating disc into relatively small droplets of coating material. As the coated particles are dispersed by the rotating disc, they are solidified by exposure to air, and are separated by sieving. FIGS. 13–15 of the patent illustrate various conical and cup shaped forms of the rotary disc.

The Iguchi et al. patent describes a process and apparatus for producing immobilized enzyme granules, by forming drops of a gellable enzyme-containing liquid with a rotating disc, and bringing the drops in contact with a gelling solution. The disc is contained in a column, and the gelling solution flows down the walls of the column to a reservoir.

Drops of the enzyme-containing liquid from the rotating disc contact the gelling solution while flowing down the walls and are carried to the reservoir.

Other encapsulation methods have comprised a procedure for forming droplets of the encapsulating medium and the biological material and a procedure for solidifying the encapsulating medium. Agarose encapsulated materials have been formed by chilling an emulsion of agarose droplets containing biological materials as shown by Nilsson et al, Nature 302:629–630 (1983) and Nilsson et al., Eur. J. Appl. Microbiol. Biotechnol. 17:319–326 (1983). Injection of droplets of polymer containing biological materials into a body of coolant such as a concurrently liquid stream has been reported by Gin et al, J.Microencapsulation 4:329–242 (1987).

Alginates form a gel when reacted with calcium ions. Alginate droplets have been formed by emulsifying a solution of sodium alginate containing cellular material to form droplets of sodium alginate and cells, and gelling the droplets with calcium chloride in U.S. Pat. No. 4,352,883. Alginate droplets have also been formed with a syringe and pump to force droplets from a needle, using a laminar flow air knife to separate droplets from the tip, the droplets being gelled by collecting them in a calcium chloride solution in U.S. Pat. No. 4,407,957. Alginate droplets have also been formed by the simple procedure of expelling them from a hypodermic needle and allowing the droplets to fall into a calcium chloride solution, as described by Nigam et al, Biotechnology Techniques 2:271–276 (1988).

Droplets have also been injected into a concurrently flowing stream containing calcium chloride in U.S. Pat. No. 3,962,383. Spraying alginate solutions through a spray nozzle to form a mist of droplets which were collected in a calcium chloride solution was reported by Plunkett et al, Laboratory Investigation 62:510–517 (1990). These methods have not proven effective for mass production of coatings required for successful transplantation.

Hommel et al. in U.S. Pat. No. 4,789,550 disclose the formation of alginate droplets using a combination of a needle and a square wave electrical electrostatic voltage to form uniform droplets. The alginate solution is forced from the tip of a needle to form a droplet, and the droplet is pulled from the needle by a changing electrostatic field between the needle tip and a calcium chloride solution placed below the needle tip. The droplet receives a charge of one polarity from the needle, opposite to the charge in the calcium chloride solution. When the voltage difference between the droplet and the oppositely charged calcium chloride solution reaches a value at which the attraction by the solution on the droplet exceeded the force of interfacial tension holding the droplet on the needle tip, the droplet is pulled free to fall into the calcium chloride solution. The electrostatic field is fluctuated using a square wave form to create a succession of voltages crossing the threshold voltage at which droplets are pulled free from the needle, thus producing a continuous series of droplets, one per square wave cycle. The process is not found to provide the small droplets and thin coatings required for effective transplantation.

There is still an unsatisfied need for an encapsulation apparatus which efficiently produces single or multiple coatings with a high degree of control and reproducibility, at a rapid rate. The encapsulation apparatus should also be effective for production of coatings required for successful biological cellular or tissue transplantation, such that the coatings have a small reproducible thickness.

SUMMARY

It is therefore an object of the present invention to provide a spin encapsulation apparatus and process for coating biological materials such as tissues, cells and cell lines with a thin semi-permeable bio-compatible coating.

It is another object of the present invention to provide a spin encapsulation apparatus and process for providing thin, uniform, continuous coatings of biological tissues, cells, cell lines and other solid and semi-solid biological and non-biological particles.

It is yet another object of the present invention to provide a spin encapsulation apparatus and process for producing such coatings with a high degree of control and reproducibility at a rapid rate, in order to enable the mass production of microcapsules, It is still another object of the present invention to provide a spin encapsulation apparatus and process which enable the precise control of the coating thickness and the overall diameter of the coated particles, and which enable the efficient generation of one or multiple coatings with smooth outer surfaces.

It is a further object of the present invention to provide a spin encapsulation apparatus and process which apply a thin coating on pancreatic islet cells, to form encapsulated insulin producing tissues for transplantation into diabetic patients.

It is another object of the present invention to provide a spin encapsulation apparatus and process for producing coatings on transplantation tissues, cells and cell lines, the coatings having a reproducible thickness of less than 200 μm.

It is yet another object of this invention to provide a spin encapsulation apparatus and process which produce coatings of physiologically non-toxic, host-compatible materials on transplantation tissues, cells and cell lines, the coatings having the permeability required for the diffusion of nutrients and biological materials required for the long life and effective function of the transplanted tissues, cells and cell lines in the transplant host, while providing effective protection to the transplanted tissues, cells and cell lines from the host immune system.

It is still another object of the present invention to provide a spin encapsulation apparatus and process which produce thin continuous coatings of biological tissues, cells, and cell lines, to form uniform microcapsules, wherein the coatings are viable for successful biological cellular and tissue transplantation.

It is another object of the present invention to provide a spin encapsulation process and apparatus which minimize the impact of the beads or droplets as they are propelled against a capture or gelling solution.

Briefly, the above and further objects and features of the present invention are realized by providing a new spin encapsulation apparatus and process. The apparatus generally includes a rotary cup for forming beads and projecting them radially outwardly, and one or more collection basins surrounding the bead forming cup. In the preferred embodiment, the encapsulation apparatus includes a plurality of axially adjacent collection basins of different sizes which gradually increase from bottom to top. It should however be understood that the sizes of the collection basins can alternatively gradually increase from top to bottom, or follow another sizing scheme. Each collection basin includes a gelation chamber for receiving the capture solution upon rotation, and a collection chamber for receiving the capsules when the collection basin is not rotating.

The cup is adjustably rotatable about its central axis, and the collection basins are independently rotatable and positioned to collect beads projected from the cup. The cup includes a mixing chamber for receiving a supply mixture of a suspension of particles to be encapsulated and an appropriate coating solution. The mixing chamber extends into a generally diverging conically shaped sidewall, such that coating becomes thinner as the coated particles travel along the sidewall. The conically shaped sidewall includes an inner surface which can be smooth or textured for altering and controlling the thickness of the coating.

As it will explained later in more detail, the coating apparatus further includes an elevation adjustment system for adjusting the alignment of the cup with respect to the collection basins in the axial direction. The rotational speeds of the cup and the collection basins are selected so as to minimize the impact of the beads against a capture solution in the gelation chambers of the collection basins.

In use, a supply mixture is introduced into a mixing chamber of the cup. As the cup spins, the coated particles are propelled upwardly by the centrifugal force from the mixing chamber along the inner surface of the cup, and are projected radially outwardly, as beads, into a gelling or capture solution in one of the selected basins. Since the cup and the basin are simultaneously rotating, the impact of the beads against the capture solution in the selected collection basin is significantly minimized.

Therefore, the spin encapsulation apparatus and process according to the present invention are highly effective for applying continuous, smooth coatings on transplantation tissues, cells or cell lines, with a high degree of control and reproducibility and at coating rates which are medically practical. The produced microcapsules have the effective volumes and diameters required for transplantation by injection through standard needle gauges. The apparatus and process are also useful for forming small, uniform beads containing tissues, cells or cell lines suitable for biochemical manufacture of products of the tissues, cells or cell lines in suitable media.

The term "transplant", as used herein, is defined to include all living tissues, cells and cell lines, and biologically active substances intended to be implanted into the body of a host animal and the act of implanting these tissues, cells and cell lines. These tissues, cells and cell lines include, without limitation, tissue and cells removed from a donor animal, tissues, cells and cell lines obtained by incubation or cultivation of donor tissues and cells, cells obtained from viable cell lines, biologically active products of cells and tissues, and the like.

Any type of tissues, cells or cell lines for which transplantation is desired can be coated and transplanted according to this invention. The most important tissues for transplants are secretory organ tissues, where transplantation from a donor organ to a host animal is desired to at least partially replicate the donor organ's action in the host system. Preferred donor tissues are pancreatic islets, hepatic cells, neural cells, renal cortex cells, vascular endothelial cells, thyroid cells, adrenal cells, thymic cells and ovarian cells. It has been experimentally found that for secretory tissues such as pancreatic islets, the thickness of protective porous coatings should be in the range of from 20 to 200 μm. The coatings must also have the permeability required to permit effective diffusion of nutrients and other essential biological materials to the transplanted tissues and passage of transplant tissue products therefrom into the host system. The coatings preferably exclude immunologically effective concentrations of agents of the host immune system from the transplant tissue.

The apparatus of the present invention will produce transplant tissue coatings having these essential characteristics with high efficiency and product volumes required to replace or supplement an organ function in a human host.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION

Figure 1:
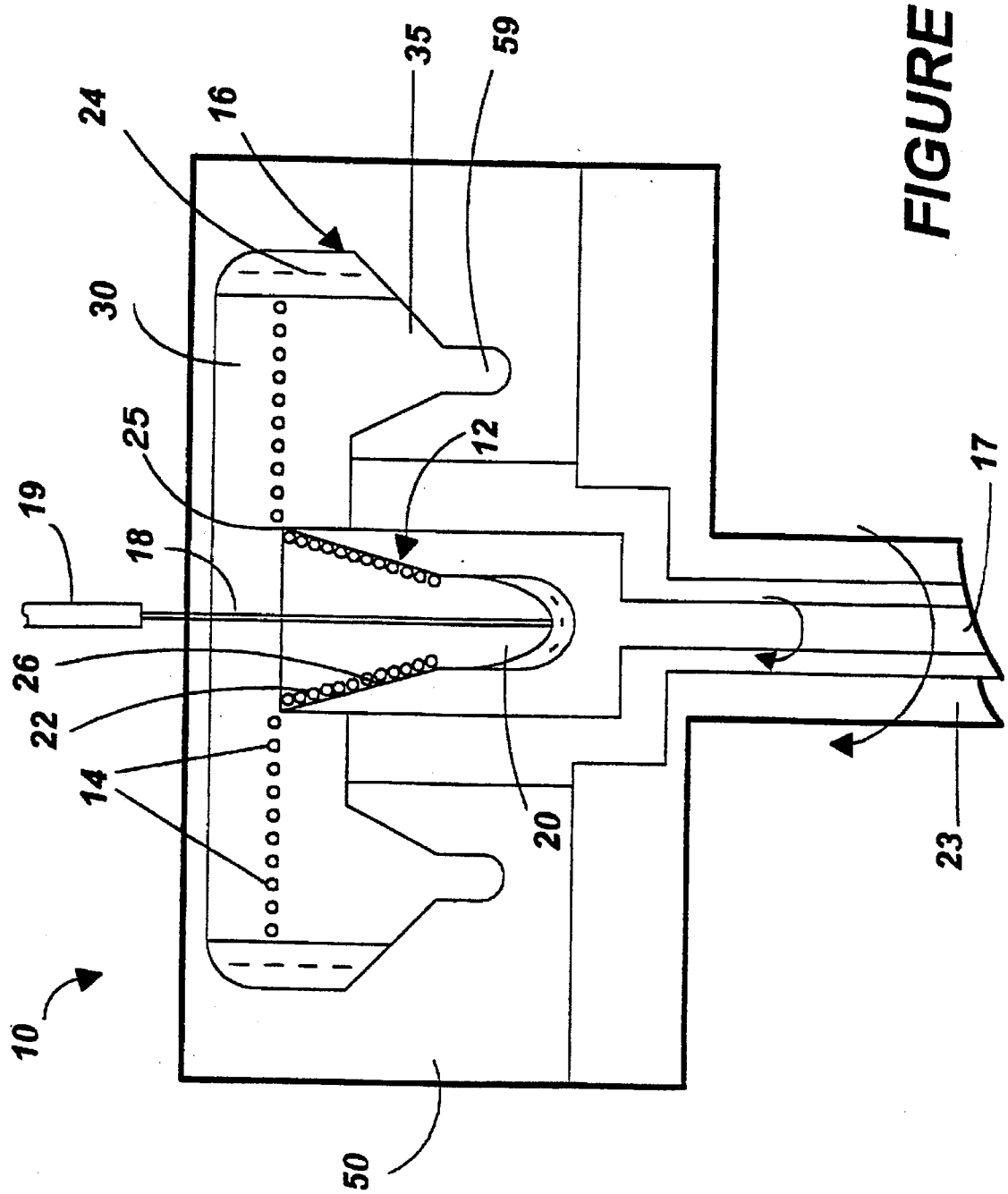
FIG. 1 is a schematic side elevational view of a simplified spin encapsulation apparatus shown in operation, and which is provided to perform an encapsulation process according to the present invention.
Figure 2:
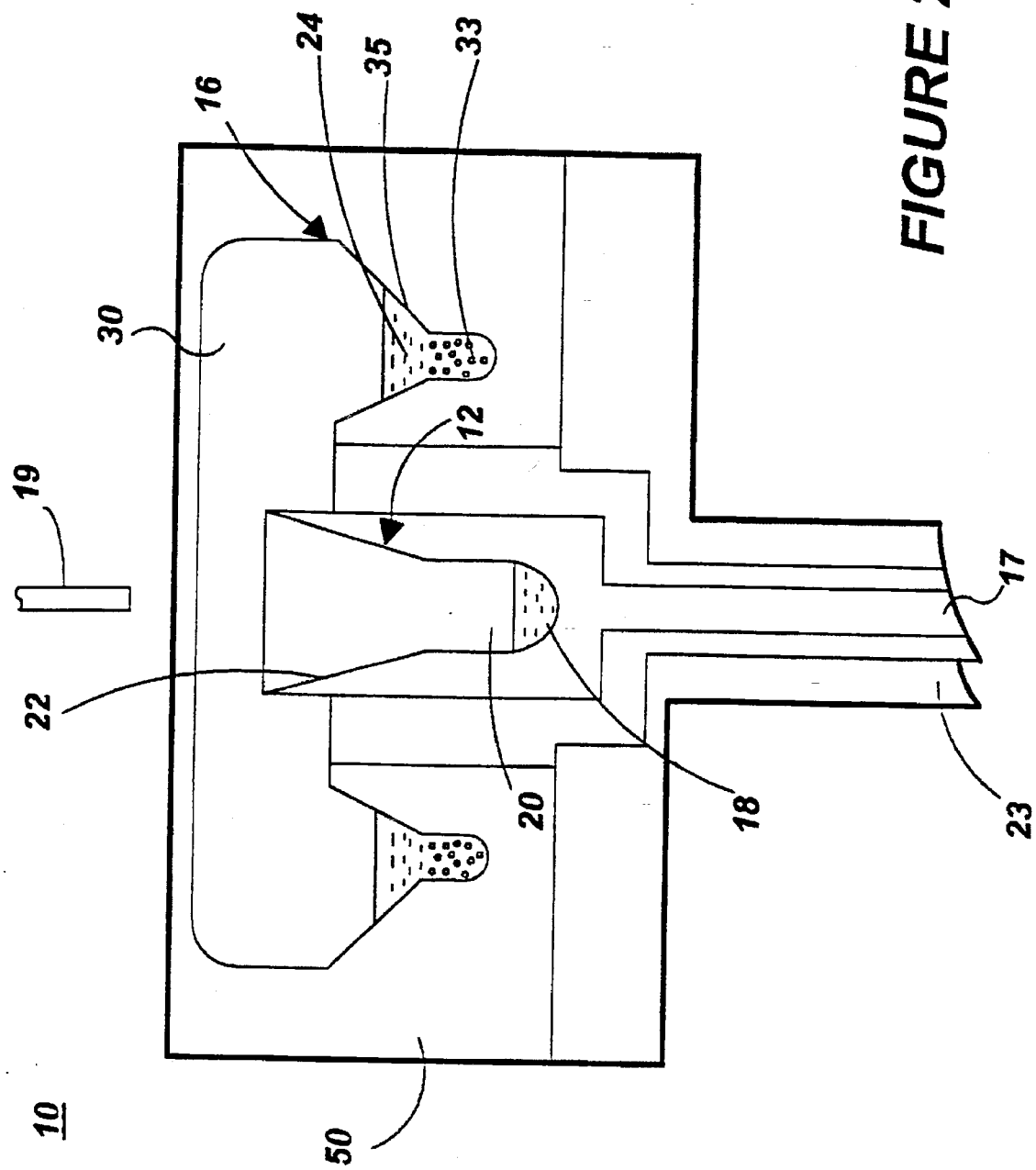
FIG. 2 is another schematic side elevational view of the spin encapsulation apparatus of FIG. 1, after the encapsulation process is completed.

Referring now to the drawings, FIGS. 1 and 2 illustrate two schematic side elevational views of a spin encapsulation apparatus 10 which is provided to perform the encapsulation process according to the present invention. The apparatus 10 generally includes a spinning disc or cup 12 for forming beads or droplets 14 and for projecting them centrifugally into a rotatable collection basin 16, which substantially surrounds the cup 12.

The cup 12 is connected to a source of rotary power, such as a motor (not shown), via a rotor or drive shaft 17, for rotation about its central axis. The cup 12 receives a supply mixture 18 of a suspension of particles, such as islet tissues, cells or cell lines, in a solution of a coating polymer, such as alginate, agarose, etc., via a conduit or tube 19, such as a syringe needle. The cup 12 includes a mixing chamber 20, which extends into an upwardly diverging, conically shaped sidewall 22, and which terminates into an upper rim or edge 25. The cup 12 is designed to project the beads 14 radially outwardly along a generally horizontal trajectory. The rotational speed of the cup 12 is adjustable.

The collection basin 16 coaxially surrounds the cup 12, for collecting the beads 14 projected by the spinning cup 12. The basin 16 is connected to a source of rotary power, such as a motor (not shown), via a rotor or drive shaft 23, for rotating about its central axis. The rotational speed of the basin 16 is also adjustable. The cup 12 and the basin 16 are independently connected to different motors, such that their rotatable speeds are separately adjustable in order to minimize the impact of the beads 14 against a gelling or capture solution 24 in the basin 16.

In use, the supply mixture 18 is introduced into the spinning cup 12, via the needle 19. The rotational speed of the cup 12 is selected to best suit the coating application. In the preferred embodiment, the rotational speed ranges between 1,000 rpm (revolutions per minute) and 30,000 rpm. It should become apparent to those skilled in the art that the rotational speeds of the cup 12 and the basin 16 can be varied during the encapsulation process, without departing from the scope of the invention.

As the cup 12 spins, the suspension surrounded by the coating is propelled by the centrifugal force from the chamber 20, and travels along the inner or bead forming surface 26 of the conical sidewall 22. The coating becomes thinner as the coated particles travel along the surface 26. It has been experimentally determined that the rotational speed of the cup 12, the travel distance of the coated particles along the surface 26, and the texture of the surface 26 determine the coating thickness, shape, and size of the final beads 14. Thus, the coating thickness decreases with the coarseness of the surface 26 and the spinning speed of the cup 12.

When the coated particles reach the upper rim 25 of the cup 12, they are projected radially outwardly, as spherical beads 14 into the gelling solution 24. The coating polymer and the gelling solution 24 are selected (i.e., alginate and CaCl2) to interact and to form solid beads or microcapsules 33 upon contact. Since the basin 16 is also spinning, the gelling solution 24 is propelled by the centrifugal force, into a lateral gelation chamber 30 which is positioned to capture the beads 14 propelled from the cup 12. The coating material is gelled, fixed or polymerized in the gelation chamber 30.

The cup 12 and the basin 16 are generally rotated in the same direction, and their rotational speeds are selected to minimize the impact of the beads 14 against the gelling solution 24, since the impact of the beads 14 against the gelling solution 24 can deform or damage the beads 14. By simultaneously rotating the cup 12 and the basin 16 in the same direction, the impact of the beads 14 against the gelling solution 24 is significantly reduced.

As illustrated in FIG. 2, after the encapsulation process is completed, the cup 12 and the basin 16 are stopped, and the flow of the supply mixture 18 is interrupted. The supply mixture 18 is collected inside the mixing chamber 20 of the cup 12, and the microcapsules 33 and the gelling solution 24 slide down from the lateral gelation chamber 30 to a collection chamber 35 of the basin 16. The microcapsules 33 are then recovered from the collection chamber 35. Fresh gelling solution 24 can be introduced into the collection chamber 35, while the apparatus 10 is stationary or after it starts rotating.

Therefore, the present invention achieves significant advantages not yet attained by the conventional encapsulation systems and methods. The present spin encapsulation apparatus 10 and process can successfully be used for coating biological materials such as tissues, cells and cell lines and other semisolid particles with a thin, uniform, continuous, and semipermeable bio-compatible coating. By using the apparatus 10, it is now possible to produce coatings with a high degree of control and reproducibility, at a rapid rate, and thus enables the mass production of microcapsules. It has been demonstrated that the encapsulation process can generate about 100,000 microcapsules in less than five minutes.

As mentioned previously, the thickness of the bead coatings can be adjusted by changing the rotational speed of the spinning cup 12, the texture of the surface 26 and/or the travel distance of the coated particles along the surface 26. The overall shape of the beads 14 can also be adjusted by changing the distance between the spinning cup 12 and the gelling chamber 30 of the collection basin 16. Additionally, the thickness and the overall diameter of the beads 14 can be adjusted by texturing the surface 26 of the conical sidewall 22 of the cup 12, and the travel distance of the coated particles along that surface 26. Thus, as the coated particles travel upwardly along the surface 26, the thickness of the coating interacts with the surface 26, and is gradually reduced.

The collected microcapsules can be recycled (i.e., by repeating the foregoing encapsulation process), in a fresh supply mixture 18 for applying one or more additional coatings on the microcapsules 33, in order to ensure that the biological particles are completely coated and encapsulated.

The preferred coating solutions are sodium alginate solutions of non-fibrogenic alginates. Other suitable coating polymers include any polymers which have the desired characteristics. The coating solutions are selected to quickly solidify or polymerize upon contact with the gelling solution 24. For example, suitable alginates polymerize upon contact with an aqueous solution containing polyvalent metal cations such as calcium and strontium ions. The gelling solution 24 is constituted to provide the component required to polymerize or solidify the polymer coating. Polysaccharides such as agarose which solidify upon contact with chilled liquid can also be used. Droplets comprising suspensions in an polyvalent metal ion solution in water can be captured in a sodium alginate solution to form encapsulated suspension. It will be readily apparent to a person skilled in the art that a wide variety of polymers can be used in the apparatus and process of this invention, and it is intended to include all suitable polymers in the use of the apparatus of this invention.

Figure 3:
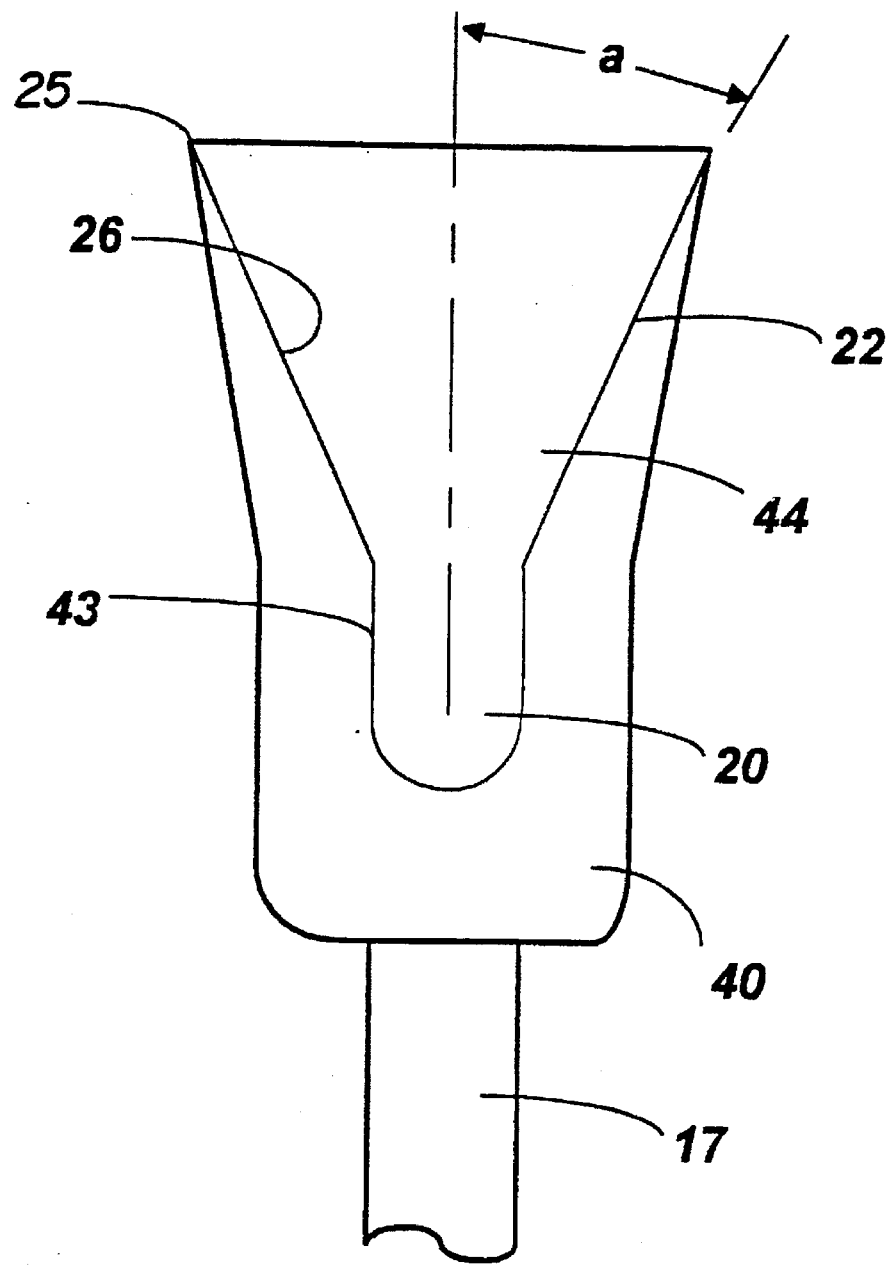
FIG. 3 is an enlarged schematic view of a cup used in the spin encapsulation apparatus of FIGS. 1 and 2.

Considering now the apparatus 10 in greater detail, FIG. 3 is an enlarged schematic view of the cup 12. The cup 12 includes a block 40 which is connected to the rotor 17 for rotating therewith. The mixing chamber 20 is defined within the block 40, for retaining the supply mixture 18. The mixing chamber 20 is hollow throughout its axial length, and is open at its upper end. In the preferred embodiment, the mixing chamber 20 includes a substantially cylindrical sidewall 43, which forms a diverging angle of less than 5 degrees with the central axis of rotation of the cup 12, which is illustrated by a broken line. It should however be understood that another inclination or angular deviation are also contemplated by the present invention. This angular deviation will allow the supply mixture 18 in the chamber 20 to progressively travel along the sidewall 43, toward the conical or beveled sidewall 22. The cup 12 can be a flat disc, V-shaped, or it can have any other appropriate shape.

Also defined within the block 40 is an upper chamber 44, which is bound by the conical sidewall 22, and which terminates, at the upper end of the block 40, in the rim or edge 25. The rim 25 can be sharp, thin or can be shaped to change the characteristics of the projected beads 14. The conical sidewall 22 forms an angle "a" with the central axis of the mixing chamber 20. The angle "a" is generally less than 90 degrees, and preferably ranges between 10 degrees and 85 degrees. The angle "a" is selected such that the conical sidewall 22 establishes a sufficient contact surface area with the coated particles, during their upward travel to the rim 25.

The inner surface 26 of the conical sidewall 22 can be smooth or roughened. Preferably, the surface 26 is roughened or textured by means of outwardly extending, shallow grooves or lines (not shown), when the angle, "a" is greater than a predetermined value, such as 70 degrees. These grooves or lines can be formed with any sharpened instrument designed for this purpose or with an abrasive material such as fine sand paper or steel wool, by moving the instrument or abrasive material across the surface 26 in the radial direction. This texturing will reduce the thickness of the coating on the particle. The cup 12 is adjustable along the vertical or axial direction, such that the beads projected from the cup 12 are directed into the gelling solution 24 in the collection basin 16. The rotational speed of the cup 12 is determined by the desired thickness of the coatings.

Figure 4:
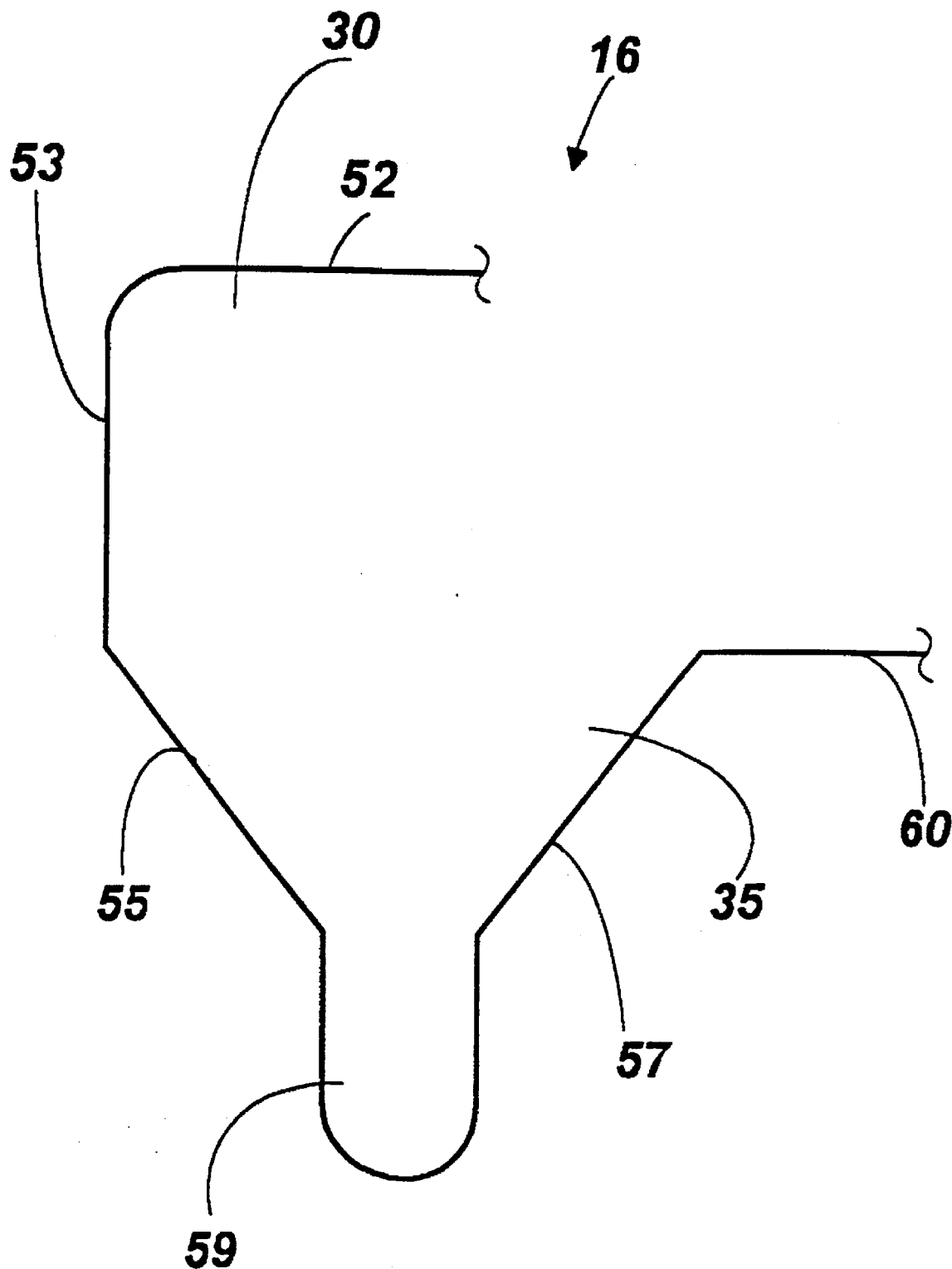
FIG. 4 is an enlarged partial schematic view of a collection basin used in the spin encapsulation apparatus of FIGS. 1 and 2.

Referring now to FIG. 4, there is illustrated a partial schematic representation of the collection basin 16. The collection basin 16 generally includes a block 50, as illustrated in FIGS. 1 and 2, which is connected to the rotor or shaft 23, for connection to a motor (not shown). The shaft 23 is preferably hollow throughout at least some of its axial length, for surrounding the shaft 17, such that both shafts 17 and 23 are independently rotatable at selected speeds.

The gelation chamber or channel 30 is defined within the block 50, and extends into the collection chamber or channel 35. The gelation chamber 30 is annular, and is defined by an upper rim or edge 52 which is substantially flat, and which extends generally horizontally and radially from the central axis into a vertical or lateral sidewall 53, which, in turn, extends into a first conical or beveled edge 55 of the collection chamber 35.

The collection chamber 35 is also annular, and is defined by the first beveled edge 55, and a second beveled edge 57, which converge into a generally U-shaped annular collection trough 59. The second beveled edge 57 is generally symmetrical to the first beveled edge 55 with respect to a central geometric axis of the trough 59. The second beveled edge 57 extends radially into a substantially flat lower rim or edge 60 parallel to the upper rim 52. The rim 60 extends inwardly toward the block 40 of the cup 12.

The rotational speed of the basin block 50 is sufficient to cause the gelling solution 24 to move travel upwardly from the collection chamber 35 and to accumulate in the gelling chamber 30. As the basin block 50 rotates, the gelling solution 24, which is initially at rest in the trough 59, is propelled by the centrifugal force along the surface of the first beveled edge 55 and accumulates against the lateral sidewall 53, within the gelation chamber 30. When the encapsulation process is completed, and the collection basin 16 stops, the gelation solution 24, containing the microcapsules 33 fall back down, along the surface of the first beveled edge 55, into the trough 59, where the microcapsules 33 are retrieved.

The apparatus 10 provides a sterile environment for the encapsulation process. In one embodiment, the basin 16 is completely enclosed, and filled with sterilized air, at room temperature, and at atmospheric pressure. It should become clear that the basin 16 can alternatively be filled with another fluid medium or ionized particles, at various temperatures and pressures to generate the desired microcapsules.

The encapsulation apparatus 10 of the present invention is particularly suitable for encapsulating or coating biological materials such as tissues, cells or cell lines. Even fragile tissues such as pancreatic islets or beta cells are not significantly disrupted when their suspension in alginate solutions are formed into beads 14 by the spinning cup 12, and the beads 14 impact the gelling solution 24 in the collection basin 16. The coatings generated by the present apparatus 10 will prevent the rejection of transplanted coated allograph and xenograph tissues. Furthermore, by using the present apparatus 10, it is possible to generate protective coatings having a thickness in the range of 20 µm to 150 µm.

The rotational speeds of the cup 12 and the basin 16 are selected so as to minimize the impact of the beads 14 as they are propelled into the gelling solution 24. In this respect, as the beads 14 leave the cup 12, they are not propelled in a strict radial way, but are rather gyrated such that the vectorial representation of their rotational speed has a radial component Vr which is generally normal to the contact surface of the gelling solution 24, and a tangential component Vt, which is perpendicular to the radial component Vr. In one embodiment according to the present invention, the rotational speed Vb of basin 16 is rendered equal to the tangential component Vt. Since the basin 16 is rotating in the same direction as the cup 12, the speed of the basin 16 relative to the tangential component Vt of the rotational speed of the cup 12 is about zero, and as a result, only the radial component Vr will affect the impact of the beads 14 against the gelling solution 24. It is also possible to minimize the radial component Vr and thus the bead impact against the gelling solution 24, by further balancing and controlling the rotational speeds of the cup 12 and the basin 16.

Figure 5:
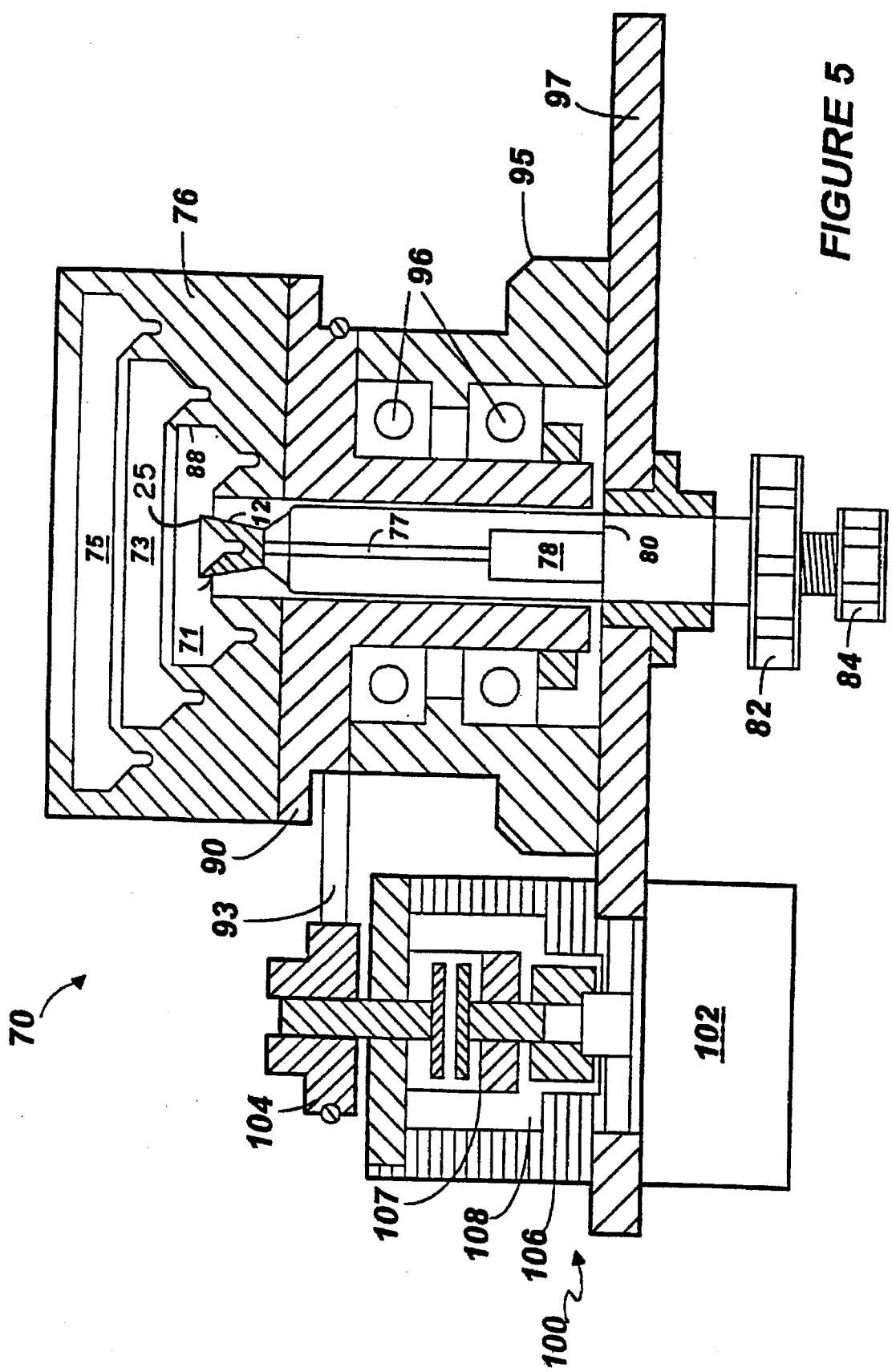
FIG. 5 is a cross-sectional view of the preferred embodiment of the spin encapsulating apparatus according to the present invention, which uses the encapsulation process of the apparatus of FIGS. 1 and 2.

Turning now to FIG. 5, there is illustrated a cross-sectional view of the preferred embodiment of a centrifugal spin encapsulating apparatus 70 according to the present invention. Components with identical numeral references to those of the apparatus 10 are similar or identical. The apparatus 70 generally includes the spinning disc or cup 12 for forming beads or droplets and for projecting them centrifugally into a selected one of a plurality of rotatable collection basins 71, 73 and 75 which substantially surround the cup 12.

The collection basins 71, 73 and 75 are formed within a single block 76. While three collection basins are shown, it should become clear that a different number of basins may alternatively be selected. The operation of the apparatus 70 is basically similar to that of the apparatus 10, and further includes the ability to select one of a plurality of collection basins 71, 73 or 75, by adjusting and aligning the cup 12 with the selected basin. The diameters of the collection chambers of the basins 71, 73 and 75 are different, preferably increasing from bottom to top. In the preferred mode, the diameters of the collection chambers can vary between 3 inches and 2 feet.

The cup 12 is mounted on a rotor or drive shaft 77, which is connected to a high speed motor 78, which can optionally be a variable speed motor. The operating speed of the motor 78 is preferably in the range from 1000 to 30,000 rpm. The motor 78 is mounted on a platform 80 connected to a conventional threaded coarse vertical adjustment wheel 82 and to a fine adjustment knob 84.

The rotation of the wheel 82 about its central axis raises or lowers the platform 80 in the vertical direction, thus axially raising or lowering the cup 12, for roughly aligning its rim 23 with a selected one of the collection basins 71, 73 or 75. The rotation of the fine adjustment knob 84 about its central axis raises or lowers the platform 80 in the axial direction, for precisely aligning the rim 23 of the cup 12 with the gelling chamber of the selected collection basin. FIG. 5 shows the rim 23 aligned with the collection basin 71. Preferably, the rim 23 is aligned with the center of the lateral sidewall 88 of the collection chamber of the selected basin, i.e., 71.

These vertical alignments can be carried out while both the cup 12 and the block 76 are rotating, and the beads are being projected from the cup 12 toward the collection basin, i.e., 71 in the present illustration. This will enable the adjustment of the elevation of the rim 23, and thus the impact level of the beads 14. In the preferred embodiment, the optimal impact level is the center of the collecting liquid surface. Additionally, with these adjustments, it is now possible to produce coatings with a high degree of control and reproductibility, at a rapid rate, thus enabling the mass production of microcapsules.

The lower collection basin 71 includes a collection chamber with the smallest diameter. The adjustment of the rim 23 can be monitored visually or by means of appropriate video equipment. It should be readily apparent to a person skilled in the art that only one or any number of the collection basins 71, 73, 75 can be used, and the shape of the lateral sidewalls of their respective collection chambers can be varied and still obtain the functional equivalent properties of the spin encapsulating apparatus 10 or 70.

In one embodiment, the collection basins 71, 73, 75 are insulated from each other, such that each basin can be used as an independent basin, similar to the basin 16 described above. Thus, for illustration purpose, while the basin 71 is filled with a first fluid medium, at predetermined temperature and pressure, any one or more of the other basins 73 and/or 75 can be filled with another fluid medium, at a different temperature. One application for this embodiment is the multi-layer coating of the particles, where a first smaller coating is deposited using one of the basins, i.e., basin 75, then a second coating is deposited using the basin 73 and the third coating is deposited using the basin 71. It should be understood that the composition of the first, second and third coatings can be similar or different.

The block 76 is mounted on a generally cylindrically shaped rotary platform 90 having a grooved rim in which a drive belt 93 is received, for imparting a rotational motion to the platform 90, and thus to the block 76 and the collection basins 71, 73 and 75 defined therein. The rotary platform 90 is supported on an outer casing 95 by means of a plurality of bearings 96. A generally flat base plate 97 supports the outer casing 95 and a motor assembly 100 for rotating the collection basins 71, 73 and 75.

The rotational speed of the motor assembly 100 can be selected by any conventional variable speed system, for example, with a variable speed motor 102 or a clutch. In the present illustration, a drive pulley 104 is connected to the drive motor 102 via a clutch 106. The clutch 106 can be any conventional speed regulating system. The clutch 106 has a flexible coupling 107 and a clutch assembly 108.

Figure 6:
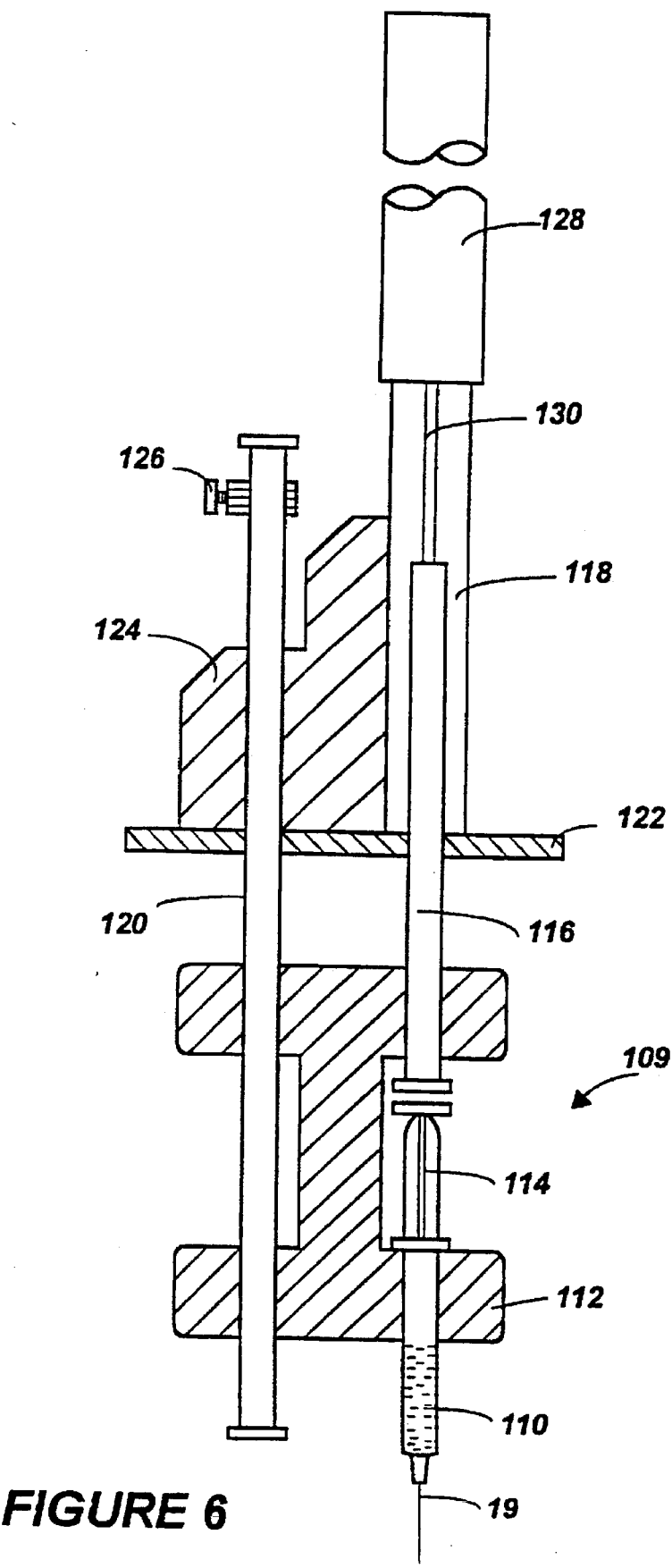
FIG. 6 is a schematic cross-sectional view of a suspension supply system according to the present invention, for use with the spin encapsulation apparatus of FIGS. 1, 2 and 5.

FIG. 6 is a cross-sectional view of one embodiment of a suspension supply system according to the present invention. The particles of islets to be encapsulated are suspended in an appropriate coating polymer solution, and are accurately metered by a syringe 109, or similar cylinder/plunger piston combination. The syringe 109 includes a barrel 110, which is supported by a clamp 112, and a plunger or piston 114 which is capable of moving telescopically within the barrel 110. A push rod 116 is mounted for vertical movement though part of the clamp 112 and through a cylindrical mount 118. The push rod 116 is positioned to depress the plunger 114 inside the barrel 110, when it is moved in the downward direction.

The clamp 112 is supported by a guide rod 120. It is secured to a mounting base 122, and extends through a reinforcement gusset 124. An adjustable stop 126 limits the downward position of the clamp 112. The gusset 124 is secured to the mounting base 122, and has a passageway through which the guide rod 120 extends. A hydraulic cylinder 128 is supported by the mount 118, and is connected to the push rod 116 by means of a rod connector 130. The downward displacement of the rod connector 130 by the hydraulic cylinder 128 causes a downward movement of the push rod 116 and thus the depression of the plunger 114, for discharging a precise flow of the suspension from the needle 19.

The operation of the apparatus of this invention is further illustrated by the following examples.

EXAMPLE 1

Preparation of High Guluronate Alginate

This example illustrates the preparation of alginates having high content of guluronate used as a first coating.

Eighty grams of protein alginate commercially available from Protan Biopolymers, Trondheim, Norway, were dissolved in 89 L water by rolling on a roller mill. The solution was filtered through a 50 micron mesh to remove particles, and then mixed on a roller mill with 320 g of bleached, activated charcoal with continued mixing for 30 minutes. The activated charcoal was then removed by centrifugation for 30 minutes. The resulting solution was sequentially filtered through filter paper, a 0.45 micron filter, a 0.22 micron filter and a 0.1 micron filter. 163 g magnesium chloride were then added to the solution and dissolved by rolling on a roller mill. 210 ml of a 1.7% calcium chloride dihydrate solution were then added and mixed by rolling on a roller mill for 30 minutes. The resulting solution was centrifuged for 30 minutes to produce an alginate pellet. The alginate pellet was dissolved in 3.0 liters of 0.1 M EDTA, pH 7.0 by rolling on a roller mill. The pH of the solution was adjusted to pH 7.0, as needed. 20 g sodium chloride were then added to this solution and dissolved.

Alginate was precipitated from the solution by the addition of 5 L of neat ethanol, followed by centrifugation for 30 minutes to obtain an alginate pellet. The alginate pellet was then suspended in ethanol and tweezed apart with tweezers to insure complete washing of the sample. Excess ethanol was then removed by squeezing and pressing the precipitate. The alginate precipitate was then dried in an oven, under vacuum, at 60° C.

These alginates were then used for coating pancreatic islets, employing the spinning disc apparatus of the present invention.

EXAMPLE 2

Preparation of High Mannuronate Alginate

This example illustrates the preparation of alginates having high content of mannuronate.

50 g low viscosity sodium alginate (LV Alginate, KELCO Div. of Merck & Co.) isolated from *Macrocystis pyrifera* were dissolved in 5 liters of water and filtered through a 50 micron mesh to remove particulates. 18.6 g tetrasodium EDTA were added to the solution and dissolved. The solution was mixed on a roller mill with 200 g hypochlorite-bleached activated charcoal (Mallinckrodt activated charcoal powder) for 30 minutes to remove organic contaminants such as polyphenols. Activated charcoal was then removed by centrifugation for 30 minutes. The resulting solution was sequentially filtered through filter paper, a 0.45 micron filter, a 0.22 micron filter and a 0.1 micron filter. 30 g sodium chloride were then added to the filtered solution and dissolved by rolling on a roller mill. The alginate was precipitated from solution by the addition of 5 L neat ethanol. The sample was centrifuged for 30 minutes to obtain an alginate pellet and the alginate pellet was suspended in ethanol and then teased apart with tweezers to insure complete washing of the sample. Excess ethanol was removed by squeezing and pressing the precipitate. The resulting precipitate was dried in an oven, under vacuum, at 60° C.

These alginates were then used for coating pancreatic islets, employing the spinning disc apparatus of the present invention.

EXAMPLE 3

Preparation of Pancreatic Islet Suspension

This example illustrates the preparation of islets in an alginate suspension. Pancreatic islets were isolated from dog by collagenase digestion using the method of Warnock G. L., Kneteman N. M., Evans M. G., et al., *Can. J. Surg.*, 33:368 (1990). The final suspension of 37,000 isolated islets in 50 ml tissue culture medium (GIBCO CMRL-1066 with 25 mM HEPES, 10% Hy Clone FBS, 2 mM L-glutamine, 100μ penicillin/ml, 100 μg streptomycin/ml) was gravity sedimented at room temperature for 15 minutes. The medium was diluted 1:2 with isotonic saline by removing 25 ml medium and replacing it with 25 ml saline. The 15 minute gravity sedimentation was repeated. The supernatant was removed to 5 ml. The islets were transferred to a 15 ml conical centrifuge tube (Corning 430055) and diluted 1:3 by the addition of 10 ml saline. After a 10 minute gravity sedimentation, the supernatant was removed and the islets resuspended in 15 ml saline. The supernatant was removed to a final volume of 0.2 ml islets in saline. 0.05 ml of 3.44% sodium citrate dihydrate with 10 mM HEPES and 2.25 ml 1% high guluronate alginate (Example 1) was added to the islet suspension giving a final concentration of 14,000 islets in 0.9% alginate in saline with 10 mM HEPES and 6 mM citrate. Note: The final suspension of islets can range from 10,000–35,000 islets/ml of 0.7–1.0% alginate.

Pancreatic islets were isolated from 10 rats using the method by Lacy P. E., Koztianvosky M. in *Diabetes*, 16:35 (1967). The 5,000 islets in 50 ml CMRL tissue culture medium were gravity sedimented at room temperature and washed with saline as for the dog above. The final supernatant was removed to 0.375 ml of islets in saline. 0.075 ml citrate and 1.05 ml 1% high guluronate alginate was added to the islet suspension giving a final concentration of 3,000 rat islets per ml of 0.7% alginate in saline with 10 mM HEPES and 6 mM citrate.

These pancreatic islet suspension are then coated employing the spinning disc apparatus of the present invention.

EXAMPLE 4

Process for Formation of First Coating

This example illustrates the process of forming the first calcium alginate coating of cell and tissue transplants.

The 14,000 dog islets suspended in 2.5 ml 0.9% high guluronate alginate prepared by the procedure of Example 3 was removed from the 15 ml centrifuge tube to a 3 ml plastic syringe by using a 16 g 2¼ inch i.v. catheter (Jelco 4062) with the needle removed. The catheter was then replaced with a 20 g blunt needle.

Using a DC electrostatic voltage of 8 KV (provided by a van de Graaff generator) between needle tip and grounded 0.117 M aqueous calcium chloride solution at ambient temperature, a suspension of pancreatic islets (14 dog islets per μl) prepared by the procedure of Example 2 was passed through a 20 gauge needle at a flow rate of approximately 200 μl/min. The suspension emerged from the needle as a thin, attenuated stream which transformed into droplets, the droplets being collected in a 60 mM petri dish (Flacon 1007) containing 10 ml calcium chloride solution. The droplets were gelled by reaction with the calcium ions in the solution. The calcium alginate coatings on the islets were smooth and uniform and had an approximate thickness of about 130 μm. The total coated particles had an average diameter of about 360 μm. This process was repeated with a suspension of 14 rat islets/μl prepared by the procedure of Example 3.

A single first coating can also be applied using the spinning disc apparatus according to the present invention, and collecting the spheres in a 100 mls of 0.120 Molar of calcium chloride.

EXAMPLE 5

Process for Preparation of Multiple Coated Pancreatic Islets Transplants with Calcium Alginate This example illustrates the process for preparation of multiple coated dog pancreatic islets transplants using an extension of the calcium alginate crosslinking.

The islets were prepared according to Example 3 and coated according to Example 4. The single coated islets in spheres were divided into two samples of 1 ml spheres per 50 ml centrifuge tube (Corning 25339-50) in the calcium chloride collecting solution. The concentration of the calcium chloride was reduced from 120 mM to 24 mM by adding 40 ml sucrose water to 10 ml of calcium chloride solution containing the 1 ml spheres. After room temperature gravity sedimentation, all fluid was removed from the spheres. To one ml of spheres, 1.5 ml sucrose water was added quickly followed by 8 ml 4% high mannuronate alginate solution (Example 2) while vortexing. The mixture was rotated in the mixing tube for at least 2 minutes to allow the halo to be formed. The outer coat was formed by using a spinning disc droplet generator, collecting the spheres in about 100 ml calcium chloride solution.

The spheres were gravity sedimented in three 50 ml centrifuge tubes. Each supernatant was removed to 15 ml so that all three could be combined into one 50 ml tube. After another gravity sedimentation, the supernatant was reduced to 15 ml, including 7.5 ml spheres, and 35 ml saline added for a dilution of 1:3. After sedimentation, the process was repeated, making a 1:10 dilution by adding 40 mls of saline to 10 mls of the solution containing the spheres. The final calcium concentration was 4–6 mM.

EXAMPLE 6

Process for Preparation of Multiple Coated Pancreatic Islet Transplants with Barium Crosslinked Alginate This example illustrates the process for preparation of multiple coated pancreatic islet transplants with barium crosslinked alginate halo.

The islets were prepared according to Example 3 and coated according to Example 4.

Excess calcium was removed from 1 ml spheres containing the islets by gravity sedimentation, removal of the supernatant, and resuspension in 15 ml sucrose water three times. Two ml 100 mM barium chloride with 10 mM HEPES was added to 10 ml sucrose water containing the spheres to reach a final concentration of 14 mM barium chloride. The sample was rotated for 5 minutes at room temperature. Excess barium was removed by washing 3 times with sucrose water as above. The supernatant was reduced to 1 ml and 3 ml 4% high mannuronate alginate (Example 2) was vortexed into the sample. The outer coat was formed by using a spinning disk droplet apparatus according to the present invention, and collecting the spheres in calcium chloride solution. The calcium chloride was diluted to 4–6 mM by washing with saline as in Example 5.

EXAMPLE 7

Process for Preparation of Multiple Coated Pancreatic Islets Transplants with Strontium Crosslinked Alginate This example illustrates the process for preparation of multiple coated pancreatic islets transplants with strontium crosslinked alginate.

The islets were prepared according to Example 3 and primary coated according to Example 4.

Soluble calcium was removed from 0.5 ml spheres containing islets by gravity sedimentation, removal of the supernatant, and resuspension in 15 ml sucrose water, repeated three times. Two ml 120 mM strontium chloride with 10 mM HEPES was added to 8 ml sucrose water containing the spheres to reach a final concentration of 24 mM. The sample was rotated for 15 minutes at room temperature using the spinning disc apparatus of the present invention. Excess strontium was removed by washing three times with sucrose waster as above.

All fluid was removed from the 0.5 ml spheres to which was added 1 ml sugar water and 2 ml 4% high mannuronate alginate (Example 2) with gentle mixing. The outer coat was formed by using the spinning disc apparatus according to the present invention, and collecting the spheres in 10 ml calcium chloride solution. The calcium chloride was diluted to 4–6 mM by washing with saline as in Example 5.

EXAMPLE 8

Transplantation of Pancreatic Islets Coated with Multiple Coating into Diabetic Mice This example illustrates the procedure used for testing the efficacy of the coated pancreatic islets in producing and delivering insulin in diabetic mice.

Host BALB/c mice were rendered diabetic by IP injection of streptozotocin (250 mg streptozocin/kg body weight) in 0.1 M citrate buffer, pH 4.5 several days prior to transplant.

Coated islets prepared by the procedure of Example 5 were injected into mice using a 16 g needle and a 3 ml syringe. Each animal received 0.2–2.0 ml spheres containing 500–2000 islets. Nine animals receiving multiple coated dog islets remained euglycemic from 54 days to 180 days. Three animals receiving double coated rat islets remained euglycemic from 63 days to 300+ days.

Empty alginate spheres were prepared at the same time and injected i.p. into three diabetic mice. Blood glucose levels remained at 350–500 mg/dL. Mice were sacrificed at intervals and the spheres examined and found to be free from fibrosis or overgrowth by macrophages.

EXAMPLE 9

Transplantation of Pancreatic Islets Coated with Multiple Coating into Diabetic Dog This example illustrates the procedure used for testing the efficacy of the coated pancreatic islets in producing and delivering insulin in diabetic dogs.

A dog was made diabetic by total pancreatectomy. Following surgery her blood glucose level was elevated to 242 mg/dL and she required 5–7 U of NPH insulin to keep it below 250 mg/dL. The animal was transplanted while under a general anesthesia. A 14 gauge angiocatheter was inserted midline into the peritoneal cavity of the dog. After removing the needle, the multiple coated islets were injected through the catheter from a 60 ml syringe. Each syringe contained 10 ml spheres in 50 ml Dulbecco's Medium.

The dog was transplanted with 94,000 multiple coated islets 8 days post pancreatectomy, 154,000 multiple coated islets 3 days later, and 54,000 double coated islets 6 days after that for a total of 300,000 islets. There were an average of 2,300 islets/ml spheres. After transplantation, the dogs' blood glucose levels were monitored several times each day. The dog was maintained on an average of 4.5 U insulin/day for two weeks post transplant. The insulin was reduced 0.5 U every two days for the next 20 days and then removed entirely from insulin therapy. The dog has remained euglycemic for 10 months to date.

EXAMPLE 10

Multiple Coating of Calcitonin Secreting Cells

This example illustrates a multiple layer coating of calcitonin secreting cells.

A suspension of calcitonin secreting cell lines MXH-5 ($2.5 \times 10^6$) were coated with alginate according to Examples 1, 2, and 4. The second coating was applied according to Example 6, using barium chloride and the spinning disc apparatus according to the present invention.

After the second coating was applied, coated capsules were tested for viability, and cell functionality by using trypan blue dry exclusion and by alamar Blue assay.

The size of these double coated capsules was determined to be within 50–199 µm (–68%). About 50% of the coated cells were viable and functional. They were able to secrete over 200 pg/ml of calcitonin which was about 50% of the amount secreted by neat uncoated cells in culture.

Other cell isolated in cell culture are coated in the same manner.

EXAMPLE 11

Multiple Coating of Hepatocytes

This example illustrates coating of isolated hepatocytes.

Hepatocytes are isolated in a manner similar to the isolation of pancreatic cells described in Example 3. Cells are then coated according to procedure described in Examples 4, 5, 6 or 7.

After the second coating is applied, the size of the coated cells is determined and the viability and functionality of the coated cells are tested.

While particular embodiments of the present invention have been disclosed, it is to be understood that various different modifications are possible and are contemplated within the scope of the specification, drawings, abstract and appended claims.

What is claimed is:

1. An encapsulation apparatus for forming capsules containing particles to be coated, the apparatus comprising in combination:

a) a rotary cup for forming beads and for projecting them centrifugally outward, said rotary cup being adjustably rotatable at a preselected first rotational speed, said rotary cup being positioned within a rotary cup block connected to a first rotor or shaft for connection to a first motor providing said first rotational speed;

b) one or more collection basins adapted for substantially surrounding said rotary cup, and being adjustably rotatable at a preselected second rotational speed,
said collection basins comprising;
a collection basin block;
an annular gelation chamber;
an annular collection chamber; and
a trough;
wherein the collection basin block is connected to a second rotor or shaft for connection to a second motor providing said second rotational speed;
wherein the annular gelation chamber is defined within the collection basin block having a substantially flat upper rim extending generally horizontally and radially from a central axis into a vertical or lateral sidewall, said sidewall extending into a first conical or beveled edge of the annular collection chamber;
wherein the collection chamber is defined by the first beveled edge and a second beveled edge, generally symmetrical to the first beveled edge, with respect to a central geometric axis of the trough and wherein the second beveled edge extends radially into a substantially flat lower rim or edge parallel to said upper rim, said lower rim extending inwardly toward the block of the rotary cup;
wherein the trough is conically shaped;
said collection basins being rotatable independently from said rotary cup and positioned to collect said beads projected from said rotary cup into a gelling solution present in the gelation chamber; and c) wherein said first and second rotational speeds are selected so as to minimize the impact of said beads against the gelling solution in said one or more collection basins.

2. The encapsulation apparatus according to claim 1, wherein said rotary cup includes a mixing chamber for receiving a supply mixture of the particles and appropriate coating material, said mixing chamber extending into a generally diverging conical sidewall forming an angle with a central axis of said mixing chamber.

3. The encapsulation apparatus according to claim 2, wherein an inner surface of said conically shaped sidewall is smooth, rough or textured.

4. The encapsulation apparatus according to claim 2, wherein said motor for said rotary cup and said motor for said collection basins are positioned to be rotatable in the same direction, such that said rotational speed of said motor for said collection basins relative to said motor for rotary cup minimizes the impact of said beads against said collection chamber sidewall in said collection basins.

5. The encapsulation apparatus according to claim 4, wherein at least one of said collection basins includes a lateral gelation chamber which is positioned to capture said beads propelled from said rotary cup; and
wherein when at least one of said collection basins is rotated, said gelling solution therein is propelled into said lateral gelation chamber for capturing said beads.

6. The encapsulation apparatus according to claim 2, consisting of at least two collection basins each of which having the gelation chamber of different size wherein the size of the gelation chamber determines the outer diameter of said beads; and wherein said outer diameter of said beads can be changed by selecting one of said collecting basins.

7. The encapsulation apparatus according to claim 3, wherein at least part of said inner surface of said conically shaped sidewall is smooth.

8. The encapsulation apparatus according to claim 3, wherein at least part of the inner surface of said conically shaped sidewall is textured.

9. The encapsulation apparatus according to claim 3, wherein said mixing chamber includes a substantially cylindrical sidewall which forms a diverging angle of less than 90° with a central axis of rotation of said rotary cup.

10. The encapsulation apparatus according to claim 9, wherein said conically shaped sidewall forms an angle with said central axis of rotation of said rotary cup, and wherein said angle ranges between 10° and 85°.

11. The encapsulation apparatus according to claim 1, wherein said rotary cup block is rotatably driven by the first rotor;
wherein said collection basins block is rotatably driven by the second rotor, independent of the rotation of said rotary cup block; and
wherein said first and second rotors are coaxially disposed relative to each other.

12. An encapsulation apparatus for forming capsules containing particles to be coated, said apparatus comprising in combination:

a) spinning means for forming beads and for projecting them centrifugally outward, said spinning means being adjustably rotatable at a preselected first rotational speed;

b) collection basins adapted for substantially surrounding said spinning means, and being adjustably rotatable at a preselected second rotational speed;

c) said collection basins being rotatable independently from said spinning means and positioned to collect said beads projected from said spinning means; and d) said first and second rotational speeds being selected so as to minimize the impact of said beads against a gelling solution in said collection basins;
wherein there are two or more collection basins of different sizes; and
wherein said collection basins are adjacently vertically disposed relatively to each other, such that the sizes of said collection basins gradually increase.

13. The encapsulation apparatus according to claim 12, wherein said spinning means is cup shaped, and includes a mixing chamber for receiving a supply mixture of the particles and appropriate coating material, said apparatus further including axial elevation adjustment means for adjustably aligning said spinning means with respect to a selected one of said collection basins.

14. The encapsulation apparatus according to claim 13, further including a suspension supply system for storing the particles to be encapsulated and said coating material wherein said coating material is a coating polymer solution, said supply system accurately metering and dispensing said particles and coating polymer solution into said mixing chamber.

15. An encapsulation apparatus comprising in combination:

a) a cup-shaped member that is rotatably mounted about an axis for spinning a fluid suspension therein, said cup-shaped member having an open end and a closed end,
said closed end being a mixing chamber for receiving a suspension of the particles to be encapsulated and an encapsulating solution, said mixing chamber extending into an upper chamber bound by a conical sidewall terminating at an upper end of the block, said conical sidewall of said upper chamber forming an angle in a range between 10° and 90° degrees with a central axis of the mixing chamber, said cup-shaped member being positioned within a block connected to a first rotor for connection to a first motor providing a first rotational speed;

the first rotor coupled to said cup-shaped member for rotating said member at she first rotational speed;

b) one or more collection basins rotatably mounted about said cup-shaped member, said collection basins comprising;

a collection basin block;
an annular gelation chamber;
an annular collection chamber; and
a trough;

wherein the block is connected to a second rotor for connection to a second motor providing said second rotational speed;

wherein the annular gelation chamber is defined within the block having a substantially flat upper rim extending generally horizontally and radially from a central axis into a vertical or lateral sidewall, said sidewall extending into a first conical or beveled edge of the annular collection chamber;

wherein the collection chamber is defined by the first beveled edge and a second beveled edge generally symmetrical to the first beveled edge with respect to a central geometric axis of the trough and wherein the second beveled edge extends radially into a substantially flat lower rim or edge parallel to said upper rim, said lower rim extending inward toward the block of the rotary cup;

wherein the trough is conically shaped; said gelation chamber being adapted for containing a gelling solution, said gelation chamber being radially spaced from said open end of the cup-shaped member; and the second rotor coupled to said collection basing for rotating said collection basins at the second rotational speed, said collection basins being rotatable independently from said cup-shaped member and positioned to collect said beads projected from said rotary cup; and said first and second rotational speeds being selected so as to minimize the impact of said beads against a gelling solution present in said gelation chamber of said collection basins.

16. The apparatus of claim 15 wherein said cup-shaped member and collection basing are rotatably mounted about the same axis.

17. The apparatus of claim 16 wherein each drive comprises a tubular member that is coupled to one of said cup-shaped members and one of said basing, a portion of one of said tubular members being coaxial with a portion of the other one of said tubular members.

18. The apparatus of claim 15 wherein said rotors are operatively independent of one another.

19. The apparatus of claim 15 wherein the conical sidewall has an inner wall of a smooth, rough or textured surface and wherein said conical chamber has a diameter that increases in a direction from said closed to said open end.

20. The apparatus of claim 19 having a plurality of collection basins formed within one collection basins block, said collection basins having different diameters, said diameters increasing from bottom to top, said apparatus having adjustment and alignment means for alignment and adjustment of the cup-shaped member with a selected collection basin, and said apparatus further having the ability to select one of the plurality of the collection basins by adjusting the cup-shaped member with a selected collection basin.

21. An encapsulation apparatus comprising in combination:

a cup-shaped member that is rotatably mounted about an axis for spinning a fluid suspension therein, said cup-shaped member having an open end and a closed end;

a first drive coupled to said cup-shaped member for rotating said member at a first speed;

a basin rotatably mounted about said cup-shaped member, said basin including a chamber adapted for containing a gelling solution, said chamber being radially spaced from said open end of the cup-shaped member; and a second drive coupled to said basin for rotating said basin at a second speed, said apparatus further including a second basin that is rotatably mounted above said first basin, said second basin including a chamber, said cup-shaped member being movable from a first position where its said open end is radially spaced from said first basin chamber to a second position where its said open end is radially spaced from said second basin chamber.

22. The apparatus of claim 21 wherein the rotational axes of said basins and cup-shaped member are the same and wherein the cup-shaped member consists of a mixing chamber and an annular upper chamber.

23. The apparatus of claim 21 wherein said basins are generally annular and their diameter is increasing from bottom to top.

24. The apparatus of claim 23 wherein the inner diameter of said second basin is greater than that of said first basin and the diameters of the collection basins vary between 3 inches and 2 feet.

25. The apparatus of claim 21 further including means for delivering a fluid suspension into said cup-shaped member.

26. The apparatus of claim 21 wherein said cup-shaped member and basin are rotatably mounted about the same axis.

27. The apparatus of claim 26 wherein each drive comprises a tubular member that is coupled to one of said cup-shaped members and basins, a portion of one of said tubular members being coaxial with a portion of the other one of said tubular members.

28. The apparatus of claim 21 wherein said drives are operatively independent of one another.

29. The apparatus of claim 21 wherein said cup-shaped member includes a tubular portion between said closed and open ends, said tubular portion including an inner wall having a diameter that increases in the direction from said closed to said open end.

30. The encapsulation apparatus according to claim 10, wherein said conically shaped sidewall forms an angle with said central axis of rotation of said rotary cup, and wherein said angle ranges between 10° and 85° .

31. The encapsulation apparatus according to claim 12, having three collection basins.

32. The encapsulation apparatus according to claim 12, having two collection basins.

33. Microcapsules containing biological tissue, cells, cell lines, solid or semisolid particle materials coated with a uniform, thin, continuous and semipermeable coating having a thickness from about 20 to about 200μ and a high degree of control and reproducibility of said coating at a rapid production of said microcapsules produced by an encapsulation process comprising steps:

a) preparing a suspension comprising a material to be coated and a coating gellable polymer;

b) delivering said suspension into a mixing chamber of a rotary cup of a spinning disk apparatus;

c) forming beads of the suspension by rotating the rotary cup of the spinning disk apparatus at a preselected first rotational speed suitable to propel the suspension by a centrifugal force from the mixing chamber along a textured inner wall of a conical sidewall of the rotary cup conical sidewall thereby forming the beads;

d) projecting said beads centrifugally outwardly from the conical sidewall into a collection basin containing a gelling solution wherein said collection basin is rotating at a preselected second rotational speed selected to minimize an impact of the beads against the gelling solution;

e) gelling the gellable coating polymer; and f) recovering coated microcapsules from a collection chamber of said collection basin.

34. The microcapsules according to claim 33, wherein the coating polymer is an alginate and the gelling solution is a calcium chloride.

35. The microcapsules according to claim 34, wherein said coating has a thickness in the range from 20 to 150μ and is semipermeable.

36. The microcapsules according to claim 35 wherein the material is a biological tissue, cell or cell line.

37. The capsules according to claim 35, wherein said biological tissue is pancreatic islet cells.

* * * * *